United States Patent
Iida (10) Patent No.: US 8,933,387 B2
(45) Date of Patent: Jan. 13, 2015

(54) OPTICAL POTENTIOMETER AND MANIPULATOR

(71) Applicant: Olympus Corporation, Tokyo (JP)

(72) Inventor: Masatoshi Iida, Hachioji (JP)

(73) Assignee: Olympus Corporation, Tokyo (JP)

( * ) Notice: Subject to any disclaimer, the term of this patent is extended or adjusted under 35 U.S.C. 154(b) by 258 days.

(21) Appl. No.: 13/662,486

(22) Filed: Oct. 28, 2012

(65) Prior Publication Data

US 2013/0047770 A1    Feb. 28, 2013

Related U.S. Application Data

(63) Continuation of application No. PCT/JP2011/056281, filed on Mar. 16, 2011.

(30) Foreign Application Priority Data

Apr. 30, 2010  (JP) .................................. 2010-105753

(51) Int. Cl.
| | |
|---|---|
| *G01B 11/14* | (2006.01) |
| *G01D 5/26* | (2006.01) |
| *A61B 19/00* | (2006.01) |
| *A61B 17/29* | (2006.01) |
| *A61B 17/00* | (2006.01) |

(Continued)

(52) U.S. Cl.
CPC ................ *G01D 5/268* (2013.01); *A61B 19/22* (2013.01); *A61B 17/29* (2013.01); *A61B 2017/00398* (2013.01); *A61B 2017/00544* (2013.01); *A61B 2017/2929* (2013.01); *A61B 2019/2242* (2013.01); *A61B 2019/5259* (2013.01)
USPC ...... 250/221; 250/227.11; 600/429; 356/614; 606/1

(58) Field of Classification Search
USPC .............. 250/221, 227.11; 600/429; 356/614; 606/1
See application file for complete search history.

(56) References Cited

U.S. PATENT DOCUMENTS

| | | | |
|---|---|---|---|
| 5,807,377 A | | 9/1998 | Madhandi et al. |
| 7,914,521 B2 * | | 3/2011 | Wang et al. ....................... 606/1 |
| 2013/0050713 A1 * | | 2/2013 | Yasuda et al. ................. 356/614 |

FOREIGN PATENT DOCUMENTS

| | | |
|---|---|---|
| JP | 60-11102 | 1/1985 |
| JP | 61-51506 | 3/1986 |

(Continued)

OTHER PUBLICATIONS

International Preliminary Report on Patentability together with the Written Opinion dated Dec. 20, 2012 received in related International Application No. PCT/JP2011/056281.

(Continued)

*Primary Examiner* — Kevin Pyo
(74) *Attorney, Agent, or Firm* — Scully, Scott, Murphy & Presser, P.C.

(57) ABSTRACT

An optical potentiometer includes a metal pipe having one end closed, a metal pipe that has a relationship of a nested structure with respect to the metal pipe and guides the metal pipe movably in a longitudinal direction, a light source and an optical fiber which supply light into the metal pipe, and an optical power meter that detects a change in the amount of reflected light from inside the metal pipe. The metal pipe has a slit along the longitudinal direction. The optical power meter detects a change in the amount of reflected light from inside the metal pipe caused by a change in the opening amount of the slit caused in accordance with the movement of the metal pipe in the longitudinal direction.

16 Claims, 4 Drawing Sheets

(56) References Cited

FOREIGN PATENT DOCUMENTS

| | | |
|---|---|---|
| JP | 7-91940 | 4/1995 |
| JP | 7-151615 | 6/1995 |

OTHER PUBLICATIONS

International Search Report dated Apr. 12, 2011 corresponding to PCT/JP2011/056281.

\* cited by examiner

OPTICAL POTENTIOMETER AND MANIPULATOR

CROSS REFERENCE TO RELATED APPLICATIONS

This application is a Continuation Application of PCT Application No. PCT/JP2011/056281, filed Mar. 16, 2011 and based upon and claiming the benefit of priority from prior Japanese Patent Application No. 2010-105753, filed Apr. 30, 2010, the entire contents of all of which are incorporated herein by reference.

BACKGROUND OF THE INVENTION

1. Field of the Invention

The present invention relates to an optical potentiometer for detecting the displacement of an object and a manipulator including the optical potentiometer.

2. Description of the Related Art

A medical manipulator is used in laparoscopic or thoracoscopic surgery. The medical manipulator generally includes a joint on the distal end side and a surgical instrument (for example, the grasp portion of a forceps or the like) at a portion nearer to the distal end than the joint.

In the manipulator having such an arrangement, a power generated by a driving source (for example, a motor or the like) is transmitted to the joint by a power transmission member (for example, a linear member such as a wire) to displace the joint. Such a power transmission mechanism opens/closes the grasp portion of the forceps or changes its orientation.

Note that the manipulator incorporates a guide member. The power transmission member is provided to be movable along the guide member.

In laparoscopic or thoracoscopic surgery using such a manipulator, a small incision is made in the abdominal part or the like of a patient. A jig called a trocar is attached into the incision. A medical manipulator is inserted from the insertion opening of the trocar, and the surgical instrument is operated to perform the surgery. The insertion opening of a currently used trocar has a diameter of about 10 mm or less. Hence, the diameter of the manipulator to be inserted from the trocar needs to be smaller than the diameter of the trocar. An example of the manipulator is a long (almost 300 mm or more) multi-degree-of-freedom manipulator having a small diameter of 10 mm or less represented by a da Vinci system available from Intuitive Surgical.

As the power transmission member, a linear member is used, as described above. The manipulator of the da Vinci system also uses a power transmission member such as a wire that is formed into a small diameter (for example, about 0.5 mm) to transmit a power in a limited space with a small diameter of 10 mm or less.

A technique associated with a manipulator using such a linear small-diameter power transmission member is disclosed in, for example, U.S. Pat. No. 5,807,377. That is, the manipulator of U.S. Pat. No. 5,807,377 is a manipulator that detects the position of the surgical instrument. U.S. Pat. No. 5,807,377 discloses a technique of detecting the displacement of the joint by a potentiometer or encoder arranged near the driving source such as a motor.

However, in the manipulator disclosed in U.S. Pat. No. 5,807,377, the driving source is disposed on the rear end side of the outer sheath. For this reason, the distance between the joint and the driving source becomes long, and the power transmission member disposed on the path essentially becomes long as well.

Additionally, the linear power transmission member for transmitting the power of the driving source to the joint has a very small diameter, as described above. For this reason, the power transmission member stretches or slackens under a tension. Accordingly, an error occurs between the driving amount of the driving source and the driving amount transmitted to the joint at the distal end. That is, when detecting the displacement of the joint by the potentiometer or encoder arranged near the driving source, the moving amount of the joint cannot accurately be detected because of the stretch or slack of the power transmission member, as described above. It is therefore difficult to detect the accurate position of the distal end of the surgical instrument.

For this reason, when getting the moving amount of the joint, the moving amount of the joint is preferably detected near the joint from the viewpoint of detection accuracy. However, in a surgical operation using the manipulator, the medical manipulator is inserted from the insertion opening of the trocar, as described above. Hence, the manipulator needs to have a small diameter (for example, 10 mm or less) for practical use. It is very difficult to provide a detection means (for example, a potentiometer, an encoder, or the like) in such a manipulator.

BRIEF SUMMARY OF THE INVENTION

The present invention has been made in consideration of the above-described situations, and has as its object to provide an optical potentiometer that can be disposed even in a small-diameter tube that forms a manipulator and has a tubular shape with a small diameter, and a manipulator including the optical potentiometer.

In order to achieve the above object, according to a first aspect of the invention, there is provided an optical potentiometer comprising:

a first tubular member having one end closed;

a second tubular member that has a relationship of a nested structure with respect to the first tubular member and guides the first tubular member movably in a longitudinal direction at the other end of the first tubular member;

a light supply member held by the second tubular member;

an opening portion provided in one of the first tubular member and the second tubular member along the longitudinal direction of the tubular member and arranged at a position where an opening amount changes in accordance with movement of the first tubular member; and a sensor unit that detects a change in an amount of reflected light from inside the tubular member.

In order to achieve the above object, according to a second aspect of the invention, there is provided a manipulator comprising:

a movable portion provided on the manipulator;

a driving source configured to drive the movable portion;

a linear power transmission member that is connected to the movable portion and transmits a power of the driving source to the movable portion; and an optical potentiometer that detects a moving amount of the linear power transmission member, wherein the optical potentiometer comprising:

a first tubular member connected to the linear power transmission member to move interlockingly and having one end closed;

a second tubular member that has a relationship of a nested structure with respect to the first tubular member and guides the first tubular member movably in a longitudinal direction at the other end of the first tubular member;

a light supply member held by the second tubular member;

an opening portion provided in one of the first tubular member and the second tubular member along the longitudinal direction of the tubular member and arranged at a position where an opening amount changes in accordance with movement of the first tubular member; and a sensor unit that detects a change in an amount of reflected light from inside the tubular member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will now be described with reference to the accompanying drawings.

Figure 1:
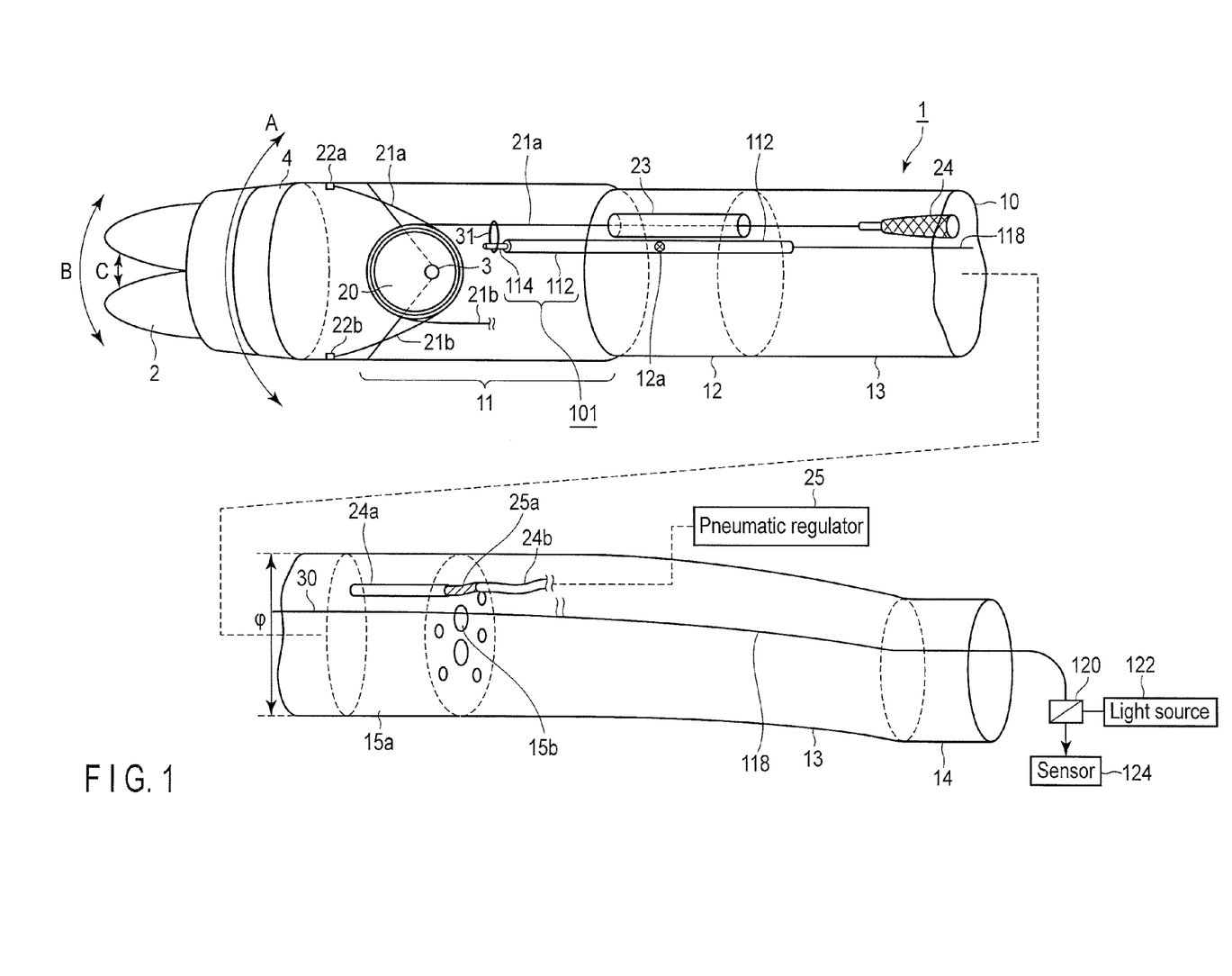
FIG. 1 is a view showing an example of the arrangement of a manipulator including an optical potentiometer according to an embodiment of the present invention.

FIG. 1 is a view showing an example of the arrangement of a medical manipulator (to be simply referred to as a manipulator hereinafter) including an optical potentiometer according to the embodiment.

A manipulator 1 comprises a grasp portion 2 that grasps, for example, a forceps or the like, a joint portion 4 configured to operate the grasp portion 2, and a storage portion 10 that is a small-diameter tube having a tubular shape with a small diameter and provided with the joint portion 4 at the distal end. The manipulator 1 is a so-called flexibility or semi-flexiblity manipulator that performs operations of 3 degrees of freedom, and details will be described later.

The joint portion 4 includes three joints. Accordingly, the grasp portion 2 performs operations of 3 degrees of freedom, that is, rotation in the direction of an arrow A about the axial direction of the manipulator 1, swing (bending) in the direction of an arrow B about an axis 3, and the grasp operation of the grasp portion 2 in the direction of an arrow C.

The joint portion 4 is provided at the distal end of the storage portion 10 that is a long small-diameter tube having a tubular shape with a small diameter and forming the manipulator 1.

Note that to avoid the illustration from becoming complex, FIG. 1 shows an arrangement for one degree of freedom, which provides the grasp portion 2 in the joint portion 4, and the grasp portion 2 swings via the joint portion 4 in the direction of the arrow B about the axis 3.

The storage portion 10 is formed by connecting a joint holding portion 11 that is a rigid portion arranged near the joint portion 4 (that is, near the distal end), a joint holding portion-side guide fixing portion 12 (to be simply referred to as a guide fixing portion 12 hereinafter), a flexible long tubular portion 13, and a proximal end fixing portion 14. The storage portion 10 that is a small-diameter tube has a diameter of at least 15 mm or less, for example, about 10 mm, and a length of about 300 mm (except the joint holding portion 11 that is a rigid portion and the guide fixing portion 12). The tubular portion 13 is formed from, for example, a resin body with metal wires being buried.

Power transmission wires 21a and 21b (to be simply referred to as wires 21a and 21b hereinafter) are stored in the storage portion 10. Each pneumatic actuator 24 is stored in the tubular portion 13 along the longitudinal direction.

Note that since the manipulator 1 originally has 3 degrees of freedom, as described above, six wires are provided in the storage portion 10, and six pneumatic actuators are provided in the tubular portion 13.

A power from each pneumatic actuator serving as a driving source is transmitted to the joint portion 4 via a wire serving as a linear power transmission member. Each joint in the joint portion 4 is thus driven.

In FIG. 1, one end of each of the wires 21a and 21b is connected to a corresponding pneumatic actuator (the pneumatic actuator to which the wire 21b is connected is not illustrated). The wires 21a and 21b are formed from, for example, SUS.

In the joint holding portion 11, a pair of pulleys 20 are rotatably juxtaposed on the same rotation axis. The other end of each of the wires 21a and 21b is wound around the pulley 20, for example, once and fixed to a corresponding one of fixing portions 22a and 22b on the rear surface of the joint portion 4. The joint holding portion 11 is made of, for example, SUS. The joint holding portion 11 holds the joint portion 4.

The wires 21a and 21b cause the grasp portion 2 to perform a one-degree-of-freedom operation of swinging in the direction of the arrow B about the axis 3. The grasp portion 2 is made to swing by moving the wires 21a and 21b in the linear direction. For example, the wire 21a is pulled, and the wire 21b is paid out, thereby causing the grasp portion 2 to swing in one direction indicated by the arrow B.

Note that the joint portion 4 includes three pairs of pulleys for bending, rotation, and grasp operation, although not illustrated to avoid the illustration from becoming complex. Each pulley is rotatably attached to a desired position in the joint holding portion 11. One wire is looped on each pulley. For example, a pneumatic actuator is connected to the proximal end portion of each wire as a driving source. When one of the two wires connected to a pair of pulleys is pulled, and the other of the two wires is paid out by pneumatic control of the pneumatic actuators, the pair of pulleys rotate in one direction. The joints in the joint portion 4 can be operated in this way. The joint portion 4 includes three joints and therefore performs an operation through three degrees of freedom (bending, rotation, and grasp).

The guide fixing portion 12 connects the joint holding portion 11 and the tubular portion 13. A power guide portion 23 is formed in the guide fixing portion 12. The power guide portion 23 is formed as a hole in the guide fixing portion 12. The wire 21a is inserted through the power guide portion 23 in the linear direction of the wire 21a. That is, the power guide portion 23 guides one wire 21a movably in the longitudinal direction.

Note that when the joint portion 4 provided with the grasp portion 2 of forceps or the like operates through three degrees of freedom, six power guide portions 23 are provided in the guide fixing portion 12 at an equal interval, for example, on a circumference of a predetermined radius.

The pneumatic actuators 24 each constituting a driving source are provided in the tubular portion 13.

The pneumatic actuator 24 is formed into a flexible thin tubular shape. The distal end of the pneumatic actuator 24 is closed. The wire 21a is connected to one end that is the closed portion. A pneumatic regulator 25 is connected to the other end. Note that to supply air controlled by the pneumatic regulator 25 into the pneumatic actuator 24, the pneumatic regulator 25 communicates with the pneumatic actuator 24 through a tube 24b (for example, urethane tube) and an actuator fluid inlet/outlet 25a (to be simply referred to as a fluid inlet/outlet 25a hereinafter).

The fluid inlet/outlet 25a is connected to the other end of the pneumatic actuator 24. Note that the fluid inlet/outlet 25a is a tube that is so long as to be inserted through an actuator fixing portion 15a and connect the tube 24b.

The pneumatic actuator 24 is fixed to the actuator fixing portion 15a by the fluid inlet/outlet 25a inserted through an actuator fixing hole 24a. The actuator fixing portion 15a is provided with an actuator fixing portion through hole 15b to pass an optical fiber 118 (light transmission tube). The pneumatic regulator 25 controls air pressure of the pneumatic actuator 24, thereby controlling movement of the wire 21a in its linear direction.

A pneumatic actuator that forms a driving source to displace the grasp portion 2 is connected to the wire 21b as well, although not illustrated. A pneumatic regulator is connected to this pneumatic actuator as well. The pneumatic regulator controls air pressure of the pneumatic actuator, thereby controlling movement of the power transmission wire 21b in its linear direction.

The pneumatic actuator 24 connected to the wire 21a and the pneumatic actuator connected to the wire 21b operate in a pair. That is, when the pneumatic actuator 24 operates to pull the wire 21a, the other pneumatic actuator operates to pay out the wire 21b. Conversely, when the pneumatic actuator 24 operates to pay out the wire 21a, the other pneumatic actuator operates to pull the wire 21b. When the pneumatic actuators are controlled in this manner, the grasp portion 2 swings in the direction of the arrow B.

Note that each pneumatic actuator is formed by a so-called McKibben scheme as a resin body in which grid-shaped like wires are buried. The wires are made of a material rigid to stretch, for example, a metal or a synthetic resin. With this arrangement, the pneumatic actuator expands and contracts in the axial direction in accordance with a change in the internal air pressure. The power transmission wire connected to the distal end of each pneumatic actuator moves by this expansion/contraction. Each pneumatic actuator is formed from a resin body and is therefore flexible.

Considering that the tubular portion 13 has a diameter of about 10 mm and a length of about 300 mm, each pneumatic actuator is formed in a diameter of about 1.5 mm and a length of almost 300 mm. This arrangement allows the tubular portion 13 to store the six pneumatic actuators, and makes it possible to obtain a power of about 10 to 20 N and a displacement of about 10 to 20 mm necessary as a manipulator by a pressure of about 0.1 to 0.6 MPa. Note that the displacement and power can be changed by adjusting parameters such as the grid angle of wires and the diameter of the actuator portion.

Note that the driving source to displace the grasp portion 2 is not limited to the pneumatic actuator 24, and any other driving source such as an actuator of another scheme, for example, a hydraulic actuator, or a motor or the like may be used.

An optical potentiometer 101 will be explained next. The optical potentiometer 101 is arranged in the guide fixing portion 12, as shown in FIG. 1. One end of the optical potentiometer 101 is connected to the wire 21a guided by the power guide portion 23.

An example of the arrangement of the optical potentiometer 101 will be described below.

Figure 2A:
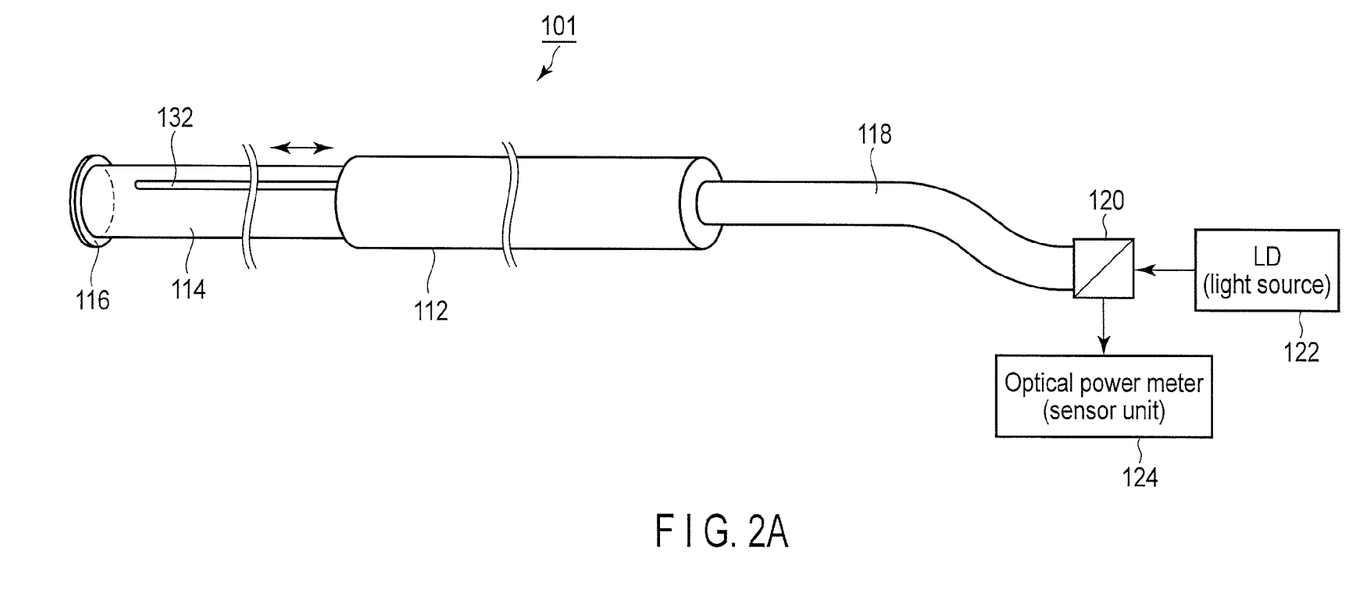
FIG. 2A is a view showing an example of the overall arrangement of an optical potentiometer according to an embodiment of the present invention.
Figure 2B:
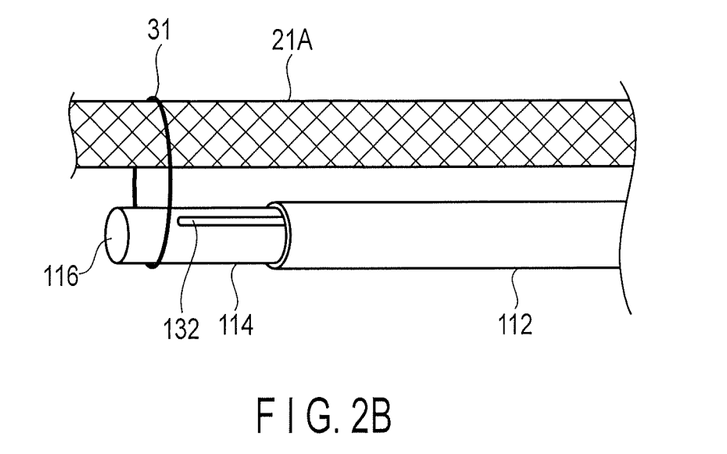
FIG. 2B is an enlarged view showing the connection portion between the optical potentiometer and a power transmission wire.
Figure 3:
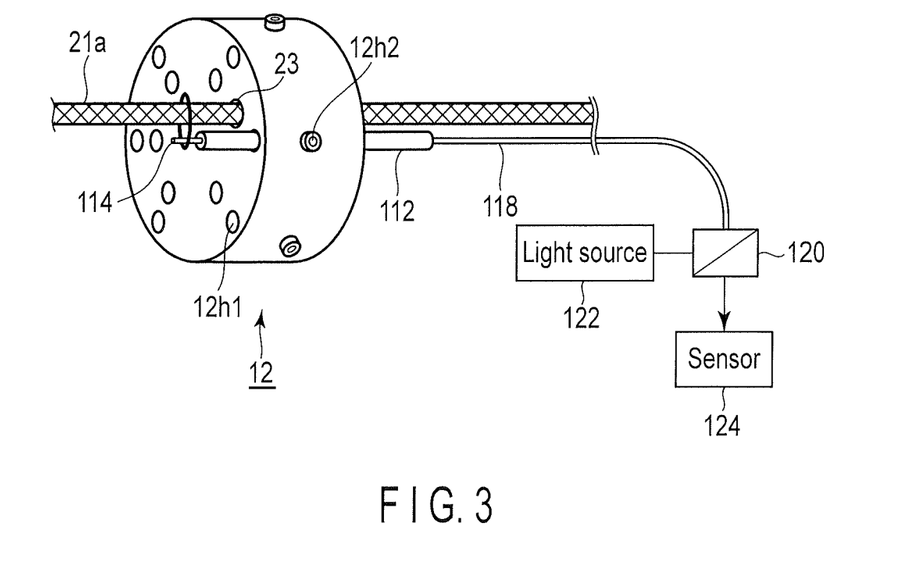
FIG. 3 is an enlarged view showing the fixed portion between the optical potentiometer and a joint holding portion-side guide fixing portion.

FIG. 2A is a view showing an example of the overall arrangement of the optical potentiometer 101. FIG. 2B is an enlarged view showing the connection portion between the optical potentiometer and a power transmission wire. FIG. 3 is an enlarged view showing the fixed portion between the optical potentiometer 101 and the guide fixing portion 12.

As shown in FIG. 2A, the optical potentiometer 101 includes a metal pipe 114 that is a first tubular member, a metal pipe 112 that is a second tubular member, a mirror member 116 that closes one end of the first tubular member, the optical fiber 118 (light supply member), a beam splitter 120, a light source 122 (light supply member), and an optical power meter 124 serving as a sensor unit.

One end of the metal pipe 114 is closed by the mirror member 116 not to leak light from both ends. The other end side of the metal pipe 114, which is not closed by the mirror member 116, is formed into a nested structure inserted into the metal pipe 112. In this embodiment, the metal pipe 114 is the inner pipe, and the metal pipe 112 is the outer pipe. The metal pipes 112 and 114 are configured to form a double structure of small-diameter thin-walled pipes each made of a metal. The metal pipe 114 on the inner side is slidable in the longitudinal direction.

The metal pipe 114 is made of a metal. At least its inner surface is formed to be able to reflect light. A slit 132 that is a thin opening portion running in the longitudinal direction is formed in the metal pipe 114, as shown in FIG. 2A. The slit 132 serves as an opening portion to output light from the light source 122 out of the metal pipe 114.

The inner diameter of the metal pipe 112 almost equals the outer diameter of the metal pipe 114 so that the metal pipes 112 and 114 are formed into a nested structure capable of being fitted with each other. Hence, light externally leaks from the metal pipe 114 only through the slit 132.

The metal pipe 114 is connected (fixed) to the outer surface of the wire 21a in the joint holding portion 11 by a connection portion 31 at a portion other than the formation position of the slit 132 (see FIG. 2B). The metal pipe 114 thus moves interlockingly with the wire 21a while externally exposing the slit 132.

Examples of the connection method using the connection portion 31 are a connection method of inserting the wire 21a and the metal pipe 114 into a heat-shrinkable annular member and applying heat to form the connection portion 31 and a connection method of forming the connection portion 31 by a solder, an adhesive, or the like. However, the present invention is not limited to these connection methods.

With this arrangement, the metal pipe 114 slides in the metal pipe 112 in its longitudinal direction interlockingly with the movement of the wire 21a. At this time, the positional relationship between the end face of the metal pipe 112 and the slit 132 of the metal pipe 114 changes in accordance with the moving amount of the wire 21a. Accordingly, the opening amount of the slit 132 changes.

The metal pipe 112 is a second tubular member that guides the metal pipe 114 movably in the longitudinal direction and changes the opening amount of the slit 132 formed in the metal pipe 114.

The metal pipe 112 has such a length that allows the metal pipe 114 to slide within a desired range in the longitudinal direction. In addition, since the metal pipe 112 is made of a metal, its inner surface can reflect light, as a matter of course. The optical fiber 118 having an outer diameter almost equal to or slightly smaller than the inner diameter of the metal pipe 112 is pressed into or bonded by an adhesive or the like to the inside the metal pipe 112 on one opening end side and fixed. That is, the metal pipe 112 and the optical fiber 118 are fixed not to externally leak light.

As described above, the optical fiber 118 is held by the metal pipe 112, and its end face enters the metal pipe 112.

The metal pipe 114 closed by the mirror member 116 is inserted, from its opening end side, into the other opening end side of the metal pipe 112. The end face of the optical fiber 118 thus faces the surface (mirror surface) of the mirror member 116.

The mirror member 116 is a closing member configured to close one end of the metal pipe 114. More specifically, the mirror member 116 is a mirror-finished member and has a disk-like shape having a diameter capable of closing at least inside the metal pipe 114. The metal pipe 114 has a mirror surface at least inside.

The optical fiber 118 is a transmission member for irradiation light from the light source (for example, LD) 122 and reflected light from inside the metal pipe 114.

The optical fiber 118 is connected to the beam splitter 120 via an optical fiber guide hole (not shown) formed in the proximal end fixing portion 14.

The beam splitter 120 receives irradiation light from the light source 122 and reflected light from inside the inner metal pipe 114 and separates them.

The light source 122 sends light into the metal pipe 114.

The optical power meter 124 serves as a sensor unit that detects (measures) a change in the amount of reflected light from inside the metal pipe 114 caused by a change in the opening amount of the slit 132 as the metal pipe 114 moves. More specifically, the optical power meter 124 measures the amount (intensity) of the reflected light separated by the beam splitter 120 from the irradiation light of the light source 122.

The optical fiber 118, the beam splitter 120, and the light source 122 form a light supply member.

As shown in FIG. 3, the guide fixing portion 12 is cylindrical. In accordance with the number of metal pipes 112, the six power guide portions 23 and six metal pipe holes 12h1 extending through in the longitudinal direction are formed in the guide fixing portion 12 circumferentially at a predetermined interval.

Each metal pipe hole 12h1 is a hole to fix a metal pipe 112 and has a diameter slightly larger than the outer shape of the metal pipe 112. The metal pipe 112 is inserted into each metal pipe hole 12h1 and fixed.

Note that the guide fixing portion 12 is provided with screw hole portions 12h2 (in FIG. 1, joint holding portion-side guide fixing parts 12a) extending through the guide fixing portion 12 from its outer surface toward the metal pipe holes 12h1. The metal pipes 112 are screwed and fixed to the guide fixing portion 12 using the screw hole portions 12h2.

One end of the metal pipe 114 is connected to the wire 21a guided by the power guide portion 23.

The operation principle of the optical potentiometer 101 will be described below.

Light from the light source 122 irradiates the inner surfaces of the metal pipes 112 and 114 via the end face of the optical fiber 118. The irradiation light is reflected by the inner surfaces of the metal pipes 112 and 114. The reflected light is reflected by the mirror portion of the mirror member 116 facing the end face of the optical fiber 118. The light reflected by the mirror portion is reflected by the inner surfaces of the metal pipes 114 and 112 and received by the end face of the optical fiber 118.

On the other hand, the light that irradiates the metal pipe 112 via the end face of the optical fiber 118 is reflected by the inner surfaces of the metal pipe 112, the mirror member 116, and the metal pipe 114. Since the slit 132 is formed in the metal pipe 114, the reflected light is partially externally output from the slit 132. That is, the light supplied from the optical fiber 118 into the metal pipe 114 externally leaks from the slit 132.

The leakage amount of the light changes in correspondence with the opening amount of the slit 132 (that is, a change in the length of the portion of the slit 132 exposed from the metal pipe 112) as the metal pipe 114 moves. As a result, the return amount of the light transmitted to the metal pipes 112 and 114 by the optical fiber 118 changes. The change in the return amount of light can be detected based on the amount of light received by the end face of the optical fiber 118.

Hence, detecting the change in the amount of light received by the end face of the optical fiber 118 allows to detect the moving amount of the metal pipe 114 in the longitudinal direction. The metal pipe 114 and the wire 21a are connected to move interlockingly with each other. It is therefore possible to detect the moving amount of the wire 21a based on the moving amount of the metal pipe 114.

The step of detecting the moving amount of the wire 21a by the optical potentiometer according to this embodiment will be described below in detail.

When the wire 21a moves, the metal pipe 114 connected to the wire 21a interlockingly moves in the metal pipe 112 in the longitudinal direction. That is, the moving amount (displacement) of the wire 21a is transmitted to the metal pipe 114, and the relative positions of the metal pipe 114 and the metal pipe 112 fixed to the guide fixing portion 12 change. As a result, the opening amount (exposure amount) of the slit 132 formed in the metal pipe 114 changes.

The change in the opening amount of the slit 132 changes the return amount of light (reflected light amount) transmitted by the optical fiber 118. The light (reflected light) reflected by the mirror member 116 and the metal pipes 114 and 112 and returned is received by the end face of the optical fiber 118 connected to the metal pipe 112 and then input to the beam splitter 120. The optical power meter 124 measures the amount (intensity) of the reflected light output from the beam splitter 120. The moving amount of the metal pipe 114 is detected based on the change in the amount of reflected light. That is, the moving amount (displacement) of the wire 21a is detected, and the displacement of the pulley is detected. In other words, the moving amount (displacement) of the grasp portion 2 is detected.

That is, in this embodiment, the moving amount of the metal pipe 114 in the longitudinal direction is detected using the change in the amount of reflected light (the amount of returned light) from inside the mirror member 116 and the metal pipes 112 and 114. Based on the detection result, the moving amount of the power transmission wire 21a and the displacement of the pulley are detected, thereby detecting the moving amount (displacement) of the grasp portion 2.

As described above, according to this embodiment, it is possible to provide an optical potentiometer that can be disposed in a small-diameter tube that has a small diameter and forms, for example, the manipulator and a manipulator including the optical potentiometer.

More specifically, according to this embodiment, the moving amount of the wire 21a can be detected based on the reflected light amount from the metal pipe 114 and the like. Hence, even when the outer shape of the metal pipe (tubular member) is made small, the moving amount of the wire 21a is rigidly affected, and the diameter of the metal pipe 114 can be reduced. It is therefore possible to arrange the optical potentiometer 101 even in a small-diameter tube having an only limited space of about, for example, 10 mm.

Since the end face of the optical fiber 118 faces the mirror member 116 that forms the closed portion of the metal pipe 114, the metal pipe 114 and the optical fiber 118 can be arranged along the longitudinal direction, and the outer shape of the optical potentiometer 101 can be made small.

The moving amount of the wire 21a (that is, the displacement of the pulley) can be detected by the simple arrangement mainly including the metal pipe 112 and the metal pipe 114 having the slit 132. In other words, the metal pipe 114 is connected to the wire 21a, thereby easily detecting the moving amount of the wire 21a.

In the above-described embodiment, the metal pipes 114 and 112 are formed as metal pipes whose inner surfaces can reflect light. However, the present invention is not limited to this arrangement. That is, the pipes need not always be made of a metal and have an inner surface formed from a mirror material as long as the inner surfaces of the pipes are configured to reflect light. For example, pipes made of a resin and having an inner surface mirror-finished using a mirror material may be used as the first tubular member and the second tubular member.

The inner/outer relationship of the nested structure of the metal pipes 114 and 112 may be reversed. That is, the diameter of the guide member (second tubular member) may be smaller than that of the guided member (first tubular member). That is, any form is possible as long as the guided member is slidable in the longitudinal direction, and the opening amount of the slit 132 changes.

In addition, the slit 132 can be formed in either the guide member (second tubular member) or the guided member (first tubular member) as long as the guided member (first tubular member) is slidable in the longitudinal direction, and the opening amount of the slit 132 changes. As long as the opening amount of the slit 132 is changed by the guide member or the guided member, both members may have the slit 132.

In the above embodiment, an arrangement has been described in which the optical fiber 118 is fixed to one opening end of the metal pipe 112. However, the present invention is not limited to this arrangement. For example, the optical fiber 118 may be fixed to the opening end on the opposite side of the mirror member 116 that closes one end of the metal pipe 114. In this case, the power transmission member is preferably connected to fix the metal pipe 114 to the guide fixing portion 12 and make the metal pipe 112 slide. In this arrangement, the inner surface of the metal pipe 112 serving as the guide member need not be light-reflective. Hence, neither a special material nor special working is necessary. In addition, the end face to which the optical fiber 118 is connected and the closed portion of the metal pipe 114 can reliably be arranged to face each other.

Note that the above embodiment has been described by exemplifying a manipulator having three degrees of freedom. However, the manipulator may have one degree of freedom or multidegree of freedom (for example, seven degrees of freedom), as a matter of course.

In the above embodiment, an example has been described in which the optical potentiometer 101 is provided in a manipulator including the flexible tubular portion 13, that is, a flexiblity or semi-flexiblity manipulator. However, the optical potentiometer 101 may be provided in a so-called rigid manipulator, as a matter of course. A pipe member may be used as the light transmission tube. A pipe member in which a relay lens and the like are arranged may be used.

As the linear power transmission member, a rod-shaped member may be used in place of a wire member such as the above-described wire 21a.

In the above embodiment, an example has been described in which the optical potentiometer 101 is applied to the manipulator 1. Instead, the embodiment may be applied to, for example, an endoscope to be bend-driven, and the optical potentiometer 101 may be connected to a linear power transmission member to bend-drive the endoscope.

That is, the optical potentiometer 101 is applicable to any device if the device includes a linear power transmission member that transmits a power from a driving source to an object.

In the above embodiment, an example has been described in which the pneumatic actuator 24 is used as the driving source. However, the present invention is not limited to this. For example, a hydraulic actuator may be used as the driving source. Alternatively, a motor may be used as the driving source.

In the above-described embodiment, the beam splitter 120 separates the irradiation light from the light source 122 and the reflected light from inside the metal pipe 114. However, in, for example, the following arrangement, the beam splitter 120 is not an essential constituent element.

Figure 4:
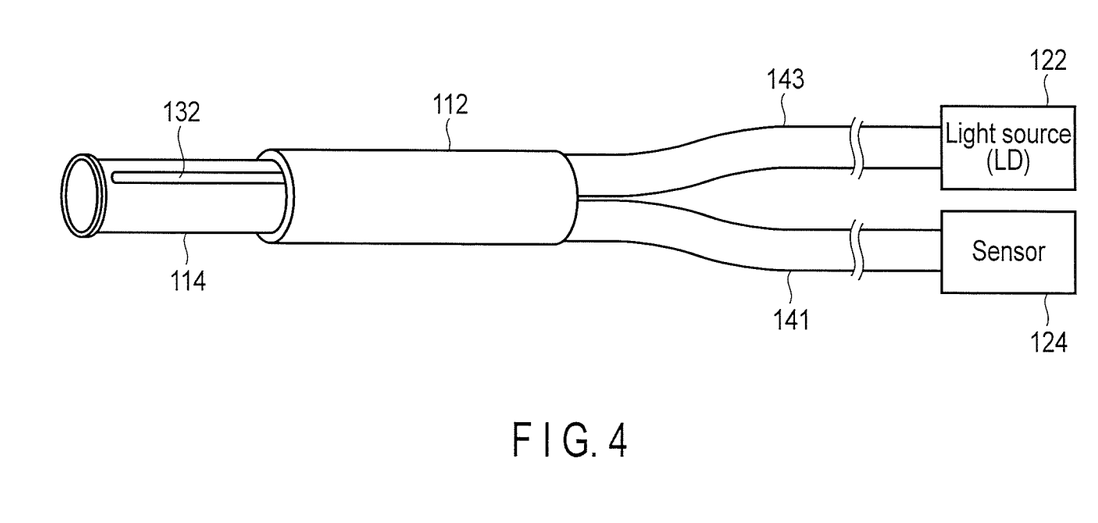
FIG. 4 is a view showing an arrangement example in which two optical fibers, that is, an optical fiber connected to only a light source to only transmit irradiation light from the light source and an optical fiber connected to only an optical power meter to only transmit reflected light from inside a metal pipe (first tubular member) are connected to an end of a metal pipe (second tubular member).

That is, for example, as shown in FIG. 4, two optical fibers, that is, an optical fiber 143 connected to only the light source 122 to only transmit irradiation light from the light source 122 and an optical fiber 141 connected to only the optical power meter 124 to only transmit reflected light from inside the metal pipe 114 (first tubular member) are connected to the end of the metal pipe 112 (second tubular member). When this arrangement is employed, the beam splitter 120 is unnecessary.

The present invention has been described above based on an embodiment. However, the present invention is not limited to the above-described embodiment, and various modifications and applications can be made without departing from the scope of the invention, as a matter of course.

[Supplementary Notes]

Inventions having the following arrangements can be extracted from the above-described embodiment.

(1) An optical potentiometer comprises:

a tubular member including a closed portion that closes one end, in which an inner surface including the closed portion is capable of reflection;

a light source that sends light into the tubular member;

an opening portion provided in the tubular member and running in the longitudinal direction to externally output the light from the light source;

a guide member that guides the tubular member movably in the longitudinal direction and changes the opening amount of the opening portion; and a sensor unit that detects (measures) a change in the amount of reflected light from inside the tubular member based on a change in the opening amount of the opening portion in accordance with movement of the tubular member.

Corresponding Embodiment

The above-described embodiment corresponds to an embodiment concerning the optical potentiometer described in (1). In this embodiment, for example, the light source 122 corresponds to the light source, for example, the metal pipe 114 corresponds to the tubular member, for example, the metal pipe 112 corresponds to the guide member, for example, the slit 132 corresponds to the opening portion, for example, the optical power meter 124 corresponds to the sensor unit, for example, the mirror member 116 corresponds to the closed portion, and, for example, the optical potentiometer 101 corresponds to the optical potentiometer.

(Functional Effects)

According to the optical potentiometer described in (1), the opening end of the opening portion changes, and the light emission amount from the light source changes as the tubular member moves. Accordingly, the amount of reflected light from inside the tubular member changes. The sensor detects (measures) the change in the reflected light amount, thereby detecting the moving amount of the tubular member in the longitudinal direction.

As described above, the moving amount of the tubular member in the longitudinal direction can be detected based on the change in the reflection amount of light in the tubular member. Since the moving amount can be detected even when the outer shape of the tubular member is made small, the diameter of the tubular member can be decreased. It is therefore possible to arrange the optical potentiometer in a small-diameter tube having a limited space.

(2) In the optical potentiometer described in (1), the sensor unit includes a light transmission tube that sends irradiation light from the light source into the tubular member and receives reflected light from inside the tubular member by the end face, and the end face of the light transmission tube is disposed to face the closed portion.

Corresponding Embodiment

The above-described embodiment corresponds to an embodiment concerning the optical potentiometer described in (2). In this embodiment, for example, the light source 122 corresponds to the light source, for example, the metal pipe 114 corresponds to the tubular member, for example, the metal pipe 112 corresponds to the guide member, for example, the slit 132 corresponds to the opening portion, for example, the optical fiber 118 corresponds to the light transmission tube, for example, the mirror member 116 corresponds to the closed portion, and, for example, the optical potentiometer 101 corresponds to the optical potentiometer.

(Functional Effects)

According to the optical potentiometer described in (2), a member for sending light from the light source into the tubular member is used as the light transmission tube, and its end face is disposed to face the closed portion of the tubular member. For this reason, the tubular member and the light transmission tube can be arrayed along the longitudinal direction, and the outer shape of the optical potentiometer can be made small even when including the light transmission tube that forms part of the sensor unit. It is therefore possible to arrange the optical potentiometer in a small-diameter tube having a limited space.

(3) In the optical potentiometer described in (1), the tubular member and the guide member are metal pipes, and the closed portion of the tubular member is formed by closing the opening portion at one end of the pipe using a mirror member having a mirror surface on the pipe side.

Corresponding Embodiment

The above-described embodiment corresponds to an embodiment concerning the optical potentiometer described in (3). In this embodiment, for example, the metal pipe 114 corresponds to the tubular member, for example, the metal pipe 112 corresponds to the guide member, and, for example, the optical potentiometer 101 corresponds to the optical potentiometer.

(Functional Effects)

According to the optical potentiometer described in (3), it is possible to attain the same effect as that of the potentiometer described in (1) and (2) with a simple arrangement.

(4) In the optical potentiometer described in (1), the tubular member is provided to move, with respect to a linear power transmission member that transmits a power from a driving source to an object, interlockingly with the linear power transmission member.

Corresponding Embodiment

The above-described embodiment corresponds to an embodiment concerning the optical potentiometer described in (4). In this embodiment, for example, the pneumatic actuator 24 corresponds to the driving source, for example, the wire 21a corresponds to the linear power transmission member, and, for example, the optical potentiometer 101 corresponds to the optical potentiometer.

(Functional Effects)

According to the optical potentiometer described in (4), since the tubular member moves interlockingly with the linear power transmission member, the moving amount of the linear power transmission member can be detected by detecting the moving amount of the tubular member.

(5) A manipulator comprises:

a long small-diameter tubular body (small-diameter tube);

a joint provided at the distal end of the tubular body;

a driving source that drives the joint;

a linear power transmission member that is connected to the joint (while being stored in the tubular body) and transmits a power from the driving source to the joint; and an optical potentiometer that detects a displacement of the joint, the optical potentiometer including:

a tubular member that is provided to move, with respect to a linear power transmission member, interlockingly with the linear power transmission member and includes a closed portion that closes one end, in which an inner surface including the closed portion is capable of reflection;

a light source that sends light into the tubular member;

an opening portion provided in the tubular member and running in the longitudinal direction to externally output the light from the light source;

a guide member that guides the tubular member movably in the longitudinal direction and changes the opening amount of the opening portion; and a sensor unit that detects (measures) a change in the amount of reflected light from inside the tubular member based on a change in the opening amount of the opening portion in accordance with movement of the tubular member.

Corresponding Embodiment

The above-described embodiment corresponds to an embodiment concerning the optical potentiometer described in (5). In this embodiment, for example, the storage portion 10 corresponds to the tubular body (small-diameter tube), for example, the joint portion 4 corresponds to the joint, for example, the pneumatic actuator 24 corresponds to the driving source, for example, the wire 21a corresponds to the linear power transmission member, for example, the light source 122 corresponds to the light source, for example, the metal pipe 114 corresponds to the tubular member, for example, the metal pipe 112 corresponds to the guide member, for example, the slit 132 corresponds to the opening portion, for example, the optical power meter 124 corresponds to the sensor unit, for example, the mirror member 116 corresponds to the closed portion, for example, the optical potentiometer 101 corresponds to the optical potentiometer, and, for example, the manipulator 1 corresponds to the manipulator.

(Functional Effects)

According to the manipulator described in (5), the moving amount of the linear power transmission member can be detected via the tubular member. Since the diameter of the tubular member can be decreased, as described above, it is possible to arrange the optical potentiometer in the small-diameter tubular body having a limited space in the manipulator.

(6) In the manipulator described in (5), the sensor unit includes a light transmission tube that sends irradiation light from the light source into the tubular member and receives reflected light from inside the tubular member by the end face, and the end face of the light transmission tube is disposed to face the closed portion.

Corresponding Embodiment

The above-described embodiment corresponds to an embodiment concerning the manipulator described in (6). In this embodiment, for example, the optical power meter 124 corresponds to the sensor unit, for example, the light source 122 corresponds to the light source, for example, the metal pipe 114 corresponds to the tubular member, for example, the metal pipe 112 corresponds to the guide member, for example, the slit 132 corresponds to the opening portion, for example, the optical fiber 118 corresponds to the light transmission tube, for example, the mirror member 116 corresponds to the closed portion, for example, the optical potentiometer 101 corresponds to the optical potentiometer, and, for example, the manipulator 1 corresponds to the manipulator.

(Functional Effects)

According to the manipulator described in (6), the outer shape of the optical potentiometer can be made small even when including the light transmission tube that forms part of the sensor unit. It is therefore possible to arrange the optical potentiometer in a small-diameter tube having a limited space in the manipulator.

(7) In the manipulator described in (5), the tubular member and the guide member are metal pipes, and the closed portion of the tubular member is formed by closing the opening portion at one end of the pipe using a mirror member having a mirror surface on the pipe side.

Corresponding Embodiment

The above-described embodiment corresponds to an embodiment concerning the manipulator described in (7). In this embodiment, for example, the metal pipe 114 corresponds to the tubular member, for example, the metal pipe 112 corresponds to the guide member, for example, the optical potentiometer 101 corresponds to the optical potentiometer, and, for example, the manipulator 1 corresponds to the manipulator.

(Functional Effects)

According to the manipulator described in (7), it is possible to attain the same effect as that of the manipulator described in (5) with a simple arrangement.

The above-described embodiment incorporates inventions of various stages, and various inventions can be extracted by appropriately combining a plurality of disclosed constituent elements. For example, if it is possible to solve the problem described in the paragraph of "problem to be solved by the invention" and obtain the effects described in the paragraph "advantages of the invention" even when several constituent elements are removed from all constituent elements of the embodiment, the arrangement without these constituent elements can also be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical potentiometer comprising:
   a first tubular member having one end closed;
   a second tubular member that has a relationship of a nested structure with respect to the first tubular member and guides the first tubular member movably in a longitudinal direction at the other end of the first tubular member;
   a light supply member held by the second tubular member;
   an opening portion provided in one of the first tubular member and the second tubular member along the longitudinal direction of the tubular member and arranged at a position where an opening amount changes in accordance with movement of the first tubular member; and
   a sensor unit that detects a change in an amount of reflected light from inside the tubular member.

2. The optical potentiometer according to claim 1, wherein the light supply member includes:
   a light source; and
   a transmission tube configured to transmit light from the light source into the first tubular member.

3. The optical potentiometer according to claim 2, wherein the transmission tube includes one of an optical fiber and a pipe member.

4. The optical potentiometer according to claim 2, wherein the transmission tube is disposed with one end face facing the closed one end of the first tubular member.

5. The optical potentiometer according to claim 1, wherein out of the first tubular member and the second tubular member, at least the tubular member arranged inside has an inner surface made of a metal material with a light reflecting surface.

6. The optical potentiometer according to claim 1, wherein out of the first tubular member and the second tubular member, at least the tubular member arranged inside has an inner surface made of a mirror material.

7. The optical potentiometer according to claim 1,
wherein out of the first tubular member and the second tubular member, at least the tubular member arranged inside has a light reflecting portion inside.

8. The optical potentiometer according to claim 1,
wherein the sensor unit detects the amount of the reflected light from inside the tubular member having the opening portion.

9. A manipulator comprising:
a movable portion provided on the manipulator;
a driving source configured to drive the movable portion;
a linear power transmission member that is connected to the movable portion and transmits a power of the driving source to the movable portion; and
an optical potentiometer that detects a moving amount of the linear power transmission member,
wherein the optical potentiometer comprising:
a first tubular member connected to the linear power transmission member to move interlockingly and having one end closed;
a second tubular member that has a relationship of a nested structure with respect to the first tubular member and guides the first tubular member movably in a longitudinal direction at the other end of the first tubular member;
a light supply member held by the second tubular member;
an opening portion provided in one of the first tubular member and the second tubular member along the longitudinal direction of the tubular member and arranged at a position where an opening amount changes in accordance with movement of the first tubular member; and
a sensor unit that detects a change in an amount of reflected light from inside the tubular member.

10. The manipulator according to claim 9,
wherein the light supply member includes:
a light source; and
a transmission tube configured to transmit light from the light source into the first tubular member.

11. The manipulator according to claim 10,
wherein the transmission tube includes one of an optical fiber and a pipe member.

12. The manipulator according to claim 10,
wherein the transmission tube is disposed with one end face facing the closed one end of the first tubular member.

13. The manipulator according to claim 9,
wherein out of the first tubular member and the second tubular member, at least the tubular member arranged inside has an inner surface made of a metal material with a light reflecting surface.

14. The manipulator according to claim 9,
wherein out of the first tubular member and the second tubular member, at least the tubular member arranged inside has an inner surface made of a mirror material.

15. The manipulator according to claim 9,
wherein out of the first tubular member and the second tubular member, at least the tubular member arranged inside has a light reflecting portion inside.

16. The manipulator according to claim 9,
wherein the sensor unit detects the amount of the reflected light from inside the tubular member having the opening portion.

* * * * *